United States Patent
Thubrikar et al.

(10) Patent No.: US 6,544,285 B1
(45) Date of Patent: Apr. 8, 2003

(54) AORTIC ROOT PROSTHESIS WITH COMPLIANT SINUSES

(75) Inventors: Mano J. Thubrikar, Charlotte, NC (US); Francis Robicsek, Charlotte, NC (US)

(73) Assignee: Heinemen Medical Research, Inc., Charlotte, NC (US)

( * ) Notice: Subject to any disclaimer, the term of this patent is extended or adjusted under 35 U.S.C. 154(b) by 0 days.

(21) Appl. No.: 09/617,408

(22) Filed: Jul. 17, 2000

Related U.S. Application Data

(60) Provisional application No. 60/176,472, filed on Jan. 17, 2000.

(51) Int. Cl.[7] .................................................. A61F 2/06
(52) U.S. Cl. ...................................... 623/2.12; 623/2.15
(58) Field of Search ........................... 623/2.12, 2.14, 623/2.15–2.19, 2.1, 1.26, 1.28, 1.29

(56) References Cited

U.S. PATENT DOCUMENTS

| | | | |
|---|---|---|---|
| 5,139,515 A | * 8/1992 | Robicsek | 623/1.28 |
| 5,376,112 A | * 12/1994 | Duran | 623/2.1 |
| 5,489,297 A | * 2/1996 | Duran | 623/2.1 |
| 6,074,419 A | * 6/2000 | Healy et al. | 623/2.14 |

\* cited by examiner

*Primary Examiner*—David H. Willse
*Assistant Examiner*—Suzette J. Jackson
(74) *Attorney, Agent, or Firm*—Adams, Schwartz & Evans, P.A.

(57) ABSTRACT

An aortic root prosthesis for being implanted into a patient during a valve sparing surgery as a replacement for a biological aortic root segment of an ascending aorta is disclosed. The aortic root prosthesis includes a hollow, annular tube having proximal and distal ends, and an inner and outer wall. The distal end is for being attached to the ascending aorta. A plurality of sinuses are circumferentially connected to the proximal end of the tube. Each of the sinuses is adapted for being attached to the aortic wall. Each of the sinuses also includes contouring means for imparting a convex contour to an outer wall of the sinus to thereby create a space between the open leaflet and its respective sinus to prevent impact between the leaflet of the valve and the inner wall of the sinus.

12 Claims, 13 Drawing Sheets

EMBODIMENT I

31A = 32A = 33A

EMBODIMENT II

32A = 33A

31A > 32A

31A > 33A

EMBODIMENT III

32A = 33A

31A < 32A

31A < 33A

AORTIC ROOT PROSTHESIS WITH COMPLIANT SINUSES

This application relates to U.S. Provisional Patent Application Ser. No. 60/176,472, filed on Jan. 17, 2000, and claims priority to that provisional application. This invention relates generally to the field of cardiovascular surgery and more specifically to the design of an aortic root prosthesis of the type implanted into a patient during a valve sparing surgery as a replacement for a diseased aortic root segment and ascending aorta. The design of this aortic root prosthesis.is based upon the physiological principles governing how the sinuses of Valsalva contribute to normal aortic valve function.

TECHNICAL FIELD AND BACKGROUND OF THE INVENTION

First described by Italian anatomist Antonio Valsalva, the sinuses of Valsalva are slight dilations or bulges located in the wall of the aorta opposite three respective leaflets of the aortic valve. Designed to promote closure of the aortic valve upon termination of each cardiac contraction, the sinuses of Valsalva play a critical role in ensuring proper blood flow through the aorta.

Aortic root prostheses used in replacing diseased aortic roots are generally formed from fabric such as the polyester sold under the trademark HEMASHELD. The cylindrical tube is scalloped at one end to match the scalloped shape of each corresponding aortic valve leaflet to which the tube is to be attached. After attaching the scalloped end of the tube to the corresponding leaflets, the other end of the tube is attached to the aorta, thereby replacing the sinuses of Valsalva and a portion of the ascending aorta. Although this cylindrical tube prosthesis is in widespread use, the prosthesis has disadvantages. One significant disadvantage is that although the cylindrical shape of the tube approximates the geometry of the aorta, the shape fails to capture the geometry of the sinuses of Valsalva and of the associated sino-tubular ridge. The functions of the sinuses and sino-tubular ridge are thus sacrificed when the cylindrical tube prosthesis is used as an aortic root graft. Another disadvantage inherent in using the tube prosthesis is that when the aortic valve opens, the leaflets of the valve sometimes hit the wall of the tube graft, which can cause abrasion and ultimately failure of the leaflets. These disadvantages confirm that the sinuses of Valsalva are needed to prevent the leaflets from hitting the tube wall and to promote proper function of the aortic valve.

Since the sinuses of Valsalva play an important role both in closing the aortic valve and in reducing the stress on the leaflets, using the tube graft can compromise the physiological function and longevity of the aortic valve. Surgeons have often realized that using the tube graft is at best a compromise, and that a better graft having a geometry similar to that of the natural aortic root and the sinuses of Valsalva needs to be developed. Prototypes of new grafts have been tested in valve sparing operations, and their valve function studied in vitro in a left heart simulator. The design of the aortic root graft, or prosthesis, considered preferable at the present time has evolved from these experiments. When the aortic valve is attached to this aortic root prosthesis, the physiological function of the valve is the same as that seen in an intact, natural aortic root.

SUMMARY OF THE INVENTION

Therefore, it is an object of the invention to provide an aortic root prosthesis for being implanted into a patient during a valve sparing surgery as a replacement for the biological aortic root segment and an ascending aorta.

It is another object of the invention to provide an aortic root prosthesis which has a geometry similar to that of the natural aortic root.

It is another object of the invention to provide an aortic root prosthesis which preserves the geometry and physiological functions of a biological aortic root when the prosthesis is used in an aortic graft.

It is another object of the invention to provide an aortic root-prosthesis having a geometry that prevents abrasion and failure of the leaflets of the aortic valve by preventing the leaflets from repeatedly hitting the prosthesis wall.

It is another object of the invention to provide an aortic root prosthesis with sinuses having a geometry and design adapted to promote proper blood flow, thereby allowing smooth formation of vortices in a space behind each respective leaflet, which reduces formation of thrombus and emboli.

It is another object of the invention to provide an aortic root prosthesis which includes a leaflet-sinus assembly having a circular cross-section in the circumferential direction of each leaflet, thereby decreasing stress at each leaflet-graft junction.

These and other objects of the present invention are achieved in the preferred embodiments disclosed below by providing an aortic root prosthesis for being implanted into a patient during a valve sparing surgery as a replacement for a biological aortic root segment of an ascending aorta. The aortic root prosthesis includes a hollow, annular tube having proximal and distal ends and an inner and outer wall, wherein the distal end is attached to the ascending aorta. The prosthesis also includes a plurality of sinuses circumferentially connected to the-proximal end of the tube. Each of the sinuses is adapted for being attached to an aortic wall and includes contouring means for importing a convex contour to an outer wall of the sinus, thereby creating a space between the open leaflet and its respective sinus to prevent impact between the leaflet of the valve and the inner wall of the sinus as the leaflet of the valve opens.

Preferably, the annular tube and the sinuses are comprised of a polyester fabric.

According to one preferred embodiment of the invention, a plurality of Z folds are formed in and extend circumferentially around the tube.

According to another preferred embodiment of the invention, a plurality of Z folds are formed in and extend along the vertical axis of each sinus and parallel to the longitudinal axis of the tube, thereby allowing each sinus to be stretched laterally.

According to yet another preferred embodiment of the invention, the contouring means comprises at least one purse string stitched around each sinus to form two concentric loops. The loops are gathered to form a tear-drop shape, thereby deflecting the convex contour downwardly toward a free end of the sinus remote from the tube.

The purse string preferably comprises 4-0 polypropylene suture.

According to yet another preferred embodiment of the invention, at least one of the loops is stitched approximately two millimeters from the periphery of each sinus.

According to yet another preferred embodiment of the invention, the proximal end of the tube is scalloped around the edge of the proximal end at a depth of at least two millimeters, thereby permitting formation of a sino-tubular junction where each sinus connects with the proximal end of the tube along the edge.

According to yet another preferred embodiment of the invention, each sinus is connected to the proximal end of the tube by respective sino-tubular junctions spaced at equal intercommissural distances.

According to yet another preferred embodiment of the invention, each sinus is connected to the proximal end of the tube by respective sino-tubular junctions. Each of the sino-tubular junctions is spaced at respective intercommissural distances from each other, whereby a first intercommissural distance is smaller than second and third intercommissural distances.

According to yet another preferred embodiment of the invention, each sinus is connected to the proximal end of the tube by respective sino-tubular junctions. Each of the sino-tubular junctions is spaced at respective intercommissural distances, whereby a first intercommissural distance is larger than second and third intercommissural distances.

According to yet another preferred embodiment of the invention, the valve is a stentless bioprosthetic valve.

According to yet another preferred embodiment of the invention, the valve is a stented bioprosthetic valve.

According to yet another preferred embodiment of the invention, a method for replacing a biological aortic root segment of an ascending aorta in a patient during a valve sparing surgery is provided, which includes providing an aortic root valve prosthesis comprising a cylindrical fabric tube having proximal.and distal ends, wherein the distal end is adapted for attachment to the ascending aorta. A plurality of sinuses are circumferentially connected to the proximal end of the tube. Each sinus is adapted for being attached to an aortic wall. Each of the sinuses is also contoured, thereby imparting a convex contour to an outer wall of the sinus. This contour creates a space between the leaflet in its open position and the respective sinus for preventing impact between the leaflet and the inner wall of the sinus as the leaflet of the valve opens. The method further includes attaching the distal end of the aortic root valve prosthesis to the ascending aorta, and attaching each of the sinuses to a respective leaflet of the aortic valve.

According to yet another preferred embodiment of the invention, a method for assembling an aortic root prosthesis for being implanted into a patient during a valve sparing surgery as a replacement for a biological aortic root segment of an ascending aorta is disclosed, and comprises the steps of measuring the diameter of an aortic valve that is to be spared and forming a cylindrical fabric aortic tube having a proximal end and a distal end, and a diameter equal to that of the aortic valve. The method further includes forming three fabric sinuses for attachment around the periphery of the proximal end of the tube, forming a convex contour on each of the fabric sinuses, and attaching each of the fabric sinuses to the proximal end of the tube.

Preferably, the tube and the sinuses used in the method for assembling an aortic root prosthesis are formed from polyester.

According to yet another preferred embodiment of the invention, a method for assembling an aortic root prosthesis is disclosed, wherein the step of attaching each sinus to the tube comprises connecting each sinus in equally-spaced relation to the proximal end by respective sino-tubular junctions spaced at equal intercommissural distances.

According to yet another preferred embodiment of the invention, a method for assembling an aortic root prosthesis is disclosed, wherein the step of attaching each sinus to the tube comprises connecting each sinus to the proximal end by respective sino-tubular junctions. Each of the sino-tubular junctions is spaced at respective intercommissural distances from each other, whereby a first intercommissural distance is smaller than second and third intercommissural distances.

According to yet another preferred embodiment of the invention, a method for assembling an aortic root prosthesis is disclosed, wherein the step of attaching each sinus to the tube comprises connecting each sinus to the proximal end by respective sino-tubular junctions. Each of the sino-tubular junctions is spaced at respective intercommissural distances from each other whereby a first intercommissural distance is larger than second and third intercommissural distances.

According to yet another preferred embodiment of the invention, a method for assembling an aortic root prosthesis is disclosed, wherein the step of forming a convex contour on each sinus comprises the steps of stitching at least one purse string around each sinus to form two concentric loops, and gathering the loops to form a tear-drop shaped sinus, wherein the convex contour is deflected downwardly toward a free end of the sinus remote from the tube.

According to yet another preferred embodiment of the invention, a method for assembling an aortic root prosthesis is disclosed, wherein the step of stitching at least one purse string around each sinus to form two concentric loops further comprises the step of stitching one of the loops at least two millimeters from the periphery of each sinus.

According to yet another preferred embodiment of the invention, a method for assembling an aortic root prosthesis is disclosed, wherein the step of forming three intercommissural distances on the proximal end of the tube comprises the step of forming three respective scalloped-shaped edges along the proximal end at a depth of approximately two millimeters, thereby permitting formation of a sino-tubular junction where each sinus connects with the proximal end.

According to yet another preferred embodiment of the invention, a method for assembling an aortic root prosthesis is disclosed, wherein the step of forming the fabric aortic tube comprises fabricating the tube from fabric having a plurality of Z folds in and extending circumferentially around the tube.

According to yet another preferred embodiment of the invention, a method for assembling an aortic root prosthesis is disclosed, wherein the step of forming the sinuses comprises fabricating the sinuses from fabric having a plurality of Z folds in and extending along the vertical axis of each sinus and parallel to the longitudinal axis of the tube, thereby allowing each sinus to be stretched laterally.

According to yet another preferred embodiment of the invention, a method for replacing a biological aortic root segment of an ascending aorta in a patient during a valve sparing surgery is disclosed, comprising the steps of measuring the diameter of an aortic valve that is to be spared, forming a cylindrical, fabric tube having a proximal end and a distal end, and a diameter equal to that of the aortic valve, and forming three fabric sinuses for attachment to the proximal end of the tube. The method further includes the steps of forming a convex contour on each sinus, attaching each sinus to the tube and an aortic wall so that the convex contour is outwardly-facing, and in such a manner as to create a space between the respective open leaflet in its open position and the sinus to prevent impact between the leaflet and the sinus, and then attaching the distal end of the tube to the ascending aorta.

Preferably, the tube and sinuses used in the method for replacing a biological aortic root segment are formed from polyester.

According to yet another preferred embodiment of the invention, a method for replacing a biological aortic root segment of an ascending aorta is disclosed, wherein the step of attaching each sinus to the tube comprises connecting each sinus in equally-spaced relation to the proximal end by respective sino-tubular junctions spaced at equal intercommissural distances.

According to yet another preferred embodiment of the invention, a method for replacing a biological aortic root segment of an ascending aorta is disclosed, wherein the step of attaching each sinus to the tube comprises connecting each sinus to the proximal end by respective sino-tubular junctions. Each of the sino-tubular junctions is spaced at respective intercommissural distances from each other, whereby a first intercommissural distance is smaller than the second and third intercommissural distances.

According to yet another preferred embodiment of the invention, a method for replacing a biological aortic root segment of an ascending aorta is disclosed, wherein the step of attaching each sinus to the tube comprises connecting each sinus to the proximal end by respective sino-tubular junctions. Each of the sino-tubular junctions is spaced at respective intercommissural distances from each other, whereby a first intercommissural distance is larger than second and third intercommissural distances.

According to yet another preferred embodiment of the invention, a method for replacing a biological aortic root segment of an ascending aorta is disclosed, wherein the step of forming a convex contour on each sinus comprises the steps of stitching at least one purse string around each sinus to form two concentric loops, said loops gathered to form a tear-drop-shaped sinus, wherein the convex contour is deflected downwardly toward a free end of the sinus remote from the tube.

According to yet another preferred embodiment of the invention, a method for replacing a biological aortic root segment of an ascending aorta is disclosed, wherein the step of attaching each sinus on the proximal end of the tube comprises the step of forming a scalloped-shaped edge on the proximal end at a depth of approximately two millimeters, thereby permitting formation of a sino-tubular junction where each sinus connects with the proximal end.

According to yet another preferred embodiment of the invention, a method for replacing a biological aortic root segment of an ascending aorta is disclosed, wherein the step of forming the fabric aortic tube comprises fabricating the tube from fabric having a plurality of Z folds in and extending circumferentially around the tube.

According to yet another preferred embodiment of the invention, a method for replacing a biological aortic root segment of an ascending aorta is disclosed, wherein the step of forming the sinuses comprises fabricating the sinuses from fabric having a plurality of Z folds in and extending along the vertical axis of each sinus and parallel to the longitudinal axis of the tube, thereby allowing each sinus to be stretched laterally.

According to yet another preferred embodiment of the invention, a method for assembling an aortic root prosthesis for being implanted into a patient during a valve sparing surgery as a replacement for a biological aortic root segment of an ascending aorta is disclosed, comprising the steps of measuring the diameter of an aortic valve to be spared and forming a cylindrical fabric tube having a diameter equal to that of the valve to be spared. Two lengths are then cut from the tube, thereby creating a first, second and third cylinder, wherein the third cylinder forms a fabric aortic root having a proximal end and a distal end. The method further comprises the steps of cutting the first cylinder open lengthwise, thereby creating a first quadrilateral. Second and third quadrilaterals having equal lengths are cut from the first quadrilateral, thereby creating a first and second sinus from the second and third quadrilaterals. The second cylinder is then cut open lengthwise, thereby creating a fourth quadrilateral. A fifth quadrilateral having a length equal to that of the second and third quadrilaterals is then cut from the fourth quadrilateral, thereby creating a third sinus from the fifth quadrilateral. Next, excess fabric is trimmed from around the edges of each sinus, thereby creating a contour for each sinus by reducing the height and width of each sinus by at least two millimeters. A convex contour is then formed on each sinus by stitching at least one purse string around each sinus to form two concentric loops, and gathering the loops to form each sinus into a tear-drop shape, thereby deflecting a convex contour downwardly toward a free end of each sinus. Three points equal to the widths of the first, second and third sinuses, respectively, are marked around the periphery of the proximal end of the fabric aortic root. The proximal end is then scalloped to form first, second and third scallops thereon in preparation for forming sino-tubular junctions. Scalloping the proximal end in this manner also creates first, second and third respective intercommissural distances. Each of the scallops has a depth of at least two millimeters. Next, a sino-tubular junction is formed by inserting a funnel-shaped object into and through the fabric aortic root, and matching each of the first, second and third intercommissural distances to a respective first, second and third sinus. Finally, each sinus is stitched to form a respective sino-tubular junction by using a running suture beginning in the middle of each scallop, and then catching the purse-string of each sinus in a loop of the running suture, thereby creating the sino-tubular junction.

According to yet another preferred embodiment of the invention, a method for implanting an aortic root prosthesis into a patient during a valve sparing surgery as a replacement for a biological aortic root segment of an ascending aorta is disclosed comprising the steps of providing an aortic root valve prosthesis comprising a cylindrical fabric tube having proximal and distal ends, wherein the distal end is adapted for attachment to the ascending aorta, and a plurality of sinuses circumferentially connected to the proximal end of the tube. Each sinus is adapted for being attached to an aortic wall of an aortic valve which is to be spared. Each sinus also includes contouring means for imparting a convex contour to an outer wall of the respective sinus, thereby creating a space between the leaflet when the leaflet is in an open position and the respective sinus to prevent impact between the leaflet and the inner wall of the sinus as the leaflet valve opens. The method further comprises the steps of scalloping the peripheral edge of an aortic wall, thereby creating a line of leaflet attachment and leaving approximately 2–3 millimeters along the peripheral edge. Orientation sutures are then stitched at respective aortal commissures, and each of the sinuses is then stitched to a respective sino-tubular commissure and along the line of leaflet attachment, thereby attaching each sinus to the respective leaflet and producing suspension of the valve. The distal end is then sutured to the ascending aorta. Finally, first and second holes are formed in the prosthesis for attachment of left and right coronary arteries to the prosthesis. The first hole is formed in a first sinus and the second hole is formed in a second sinus. The left and right coronary arteries are then attached to respective first and second holes.

According to yet another preferred embodiment of the invention, a method for replacing a biological aortic root segment of an ascending aorta in a patient during a valve sparing surgery is disclosed comprising the steps of measuring the diameter of an aortic valve to be spared and forming a cylindrical fabric tube having a diameter equal to that of the valve to be spared. Two lengths are then cut from the tube, thereby creating a first, second and third cylinder, wherein the third cylinder forms a fabric aortic root having a proximal end and a distal end. The first cylinder is then cut open lengthwise, thereby creating a first quadrilateral. Second and third quadrilaterals having equal lengths are cut from the first quadrilateral, thereby creating a first and second sinus from the second and third quadrilaterals. The second cylinder is then cut open lengthwise, thereby creating a fourth quadrilateral. A fifth quadrilateral having a length equal to that of the second and third quadrilaterals is cut from the fourth quadrilateral thereby creating a third sinus from the fifth quadrilateral. Excess fabric is then trimmed from around the edge of each sinus, thereby creating a contour for each sinus by reducing the height and width of each sinus by at least two millimeters. The method further includes the steps of forming a convex contour on each sinus by stitching at least one purse string around each sinus to form two concentric loops and gathering said loops to form each sinus into a tear-drop shape, thereby deflecting a convex contour downwardly toward the end of each sinus. Three points equal to the widths of the first, second and third sinuses, respectively, are then measured and marked around the periphery of the proximal end of the fabric aortic root, and the proximal end is scalloped, thereby forming a first, second and third scallop on the proximal end. Each of the scallops has a depth of at least two millimeters and a corresponding first, second and third intercommissural distance. Three respective sino-tubular junctions are then formed by inserting a funnel-shaped object into and through the fabric aortic root, and matching each of the first, second and third intracommissurial distances to a respective first, second-and third sinus. Each sinus is then stitched along its respective scallop by using a running suture beginning in the middle of each scallop, and by catching the purse-string of each sinus in a loop of the running suture, thereby forming the sino-tubular junctions. Next, the peripheral edge of an aortic wall of an aortic valve that is to be spared is scalloped, thereby creating a line of leaflet attachment and leaving approximately 2–3 millimeters along the line of leaflet attachment for attaching the edge to the sinuses along the line of leaflet attachment. Orientation sutures are then stitched at respective sino-tubular commissures, and each of the sino-tubular commissures is sutured to a respective aortic commissure, thereby producing suspension of the valve. The distal end is then sutured to the ascending aorta. Finally, first and second holes are formed in the prosthesis for attachment of left and right coronary arteries to the prosthesis. The first hole is formed in a first sinus and the second hole is formed in a second sinus, and the left and right coronary arteries are then attached to the respective first and second holes.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
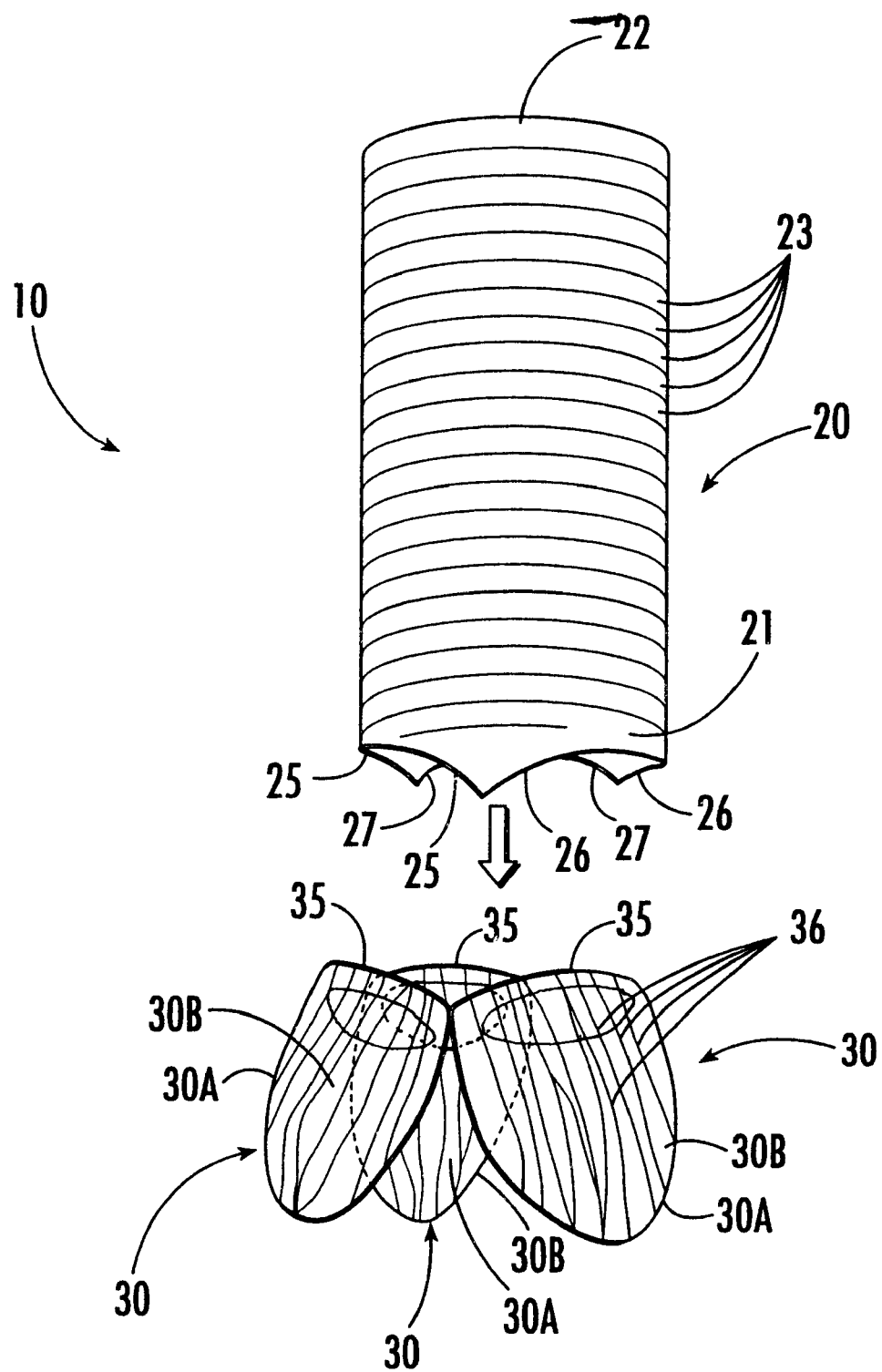
FIG. 1 is an exploded perspective view of an aortic root prosthesis during assembly according to one embodiment of the invention.

Referring now specifically to the drawings, an aortic root prosthesis according to the present invention is illustrated in FIG. 1 and shown generally at reference numeral 10. The aortic root prosthesis 10 is shown during assembly. The aortic root prosthesis 10 includes a hollow, annular tube shown generally at reference numeral 20, having proximal and distal ends 21 and 22, respectively. The tube 20 is preferably formed from polyester fabric such as that sold under the trademark DACRON, and includes a plurality of integrally-formed Z-folds 23 extending circumferentially around the tube 20. The distal end 22 is adapted for being attached to an ascending aorta. Three sinuses, each of which are shown generally at reference numeral 30, are positioned and ready for attachment of sinus edges 35 to one of three respective scalloped edges 25, 26 or 27 to form one of three respective sino-tubular junctions 31, 32 or 33. (See FIGS. 2 and 3.) The tube and sinuses 30 are preferably formed from a woven, double-velour, polyester fabric such as that sold under the trademarks DACRON and HEMASHIELD, which is coated with collagen for decreasing leakage through the prosthesis after it has been implanted.

Figure 2:
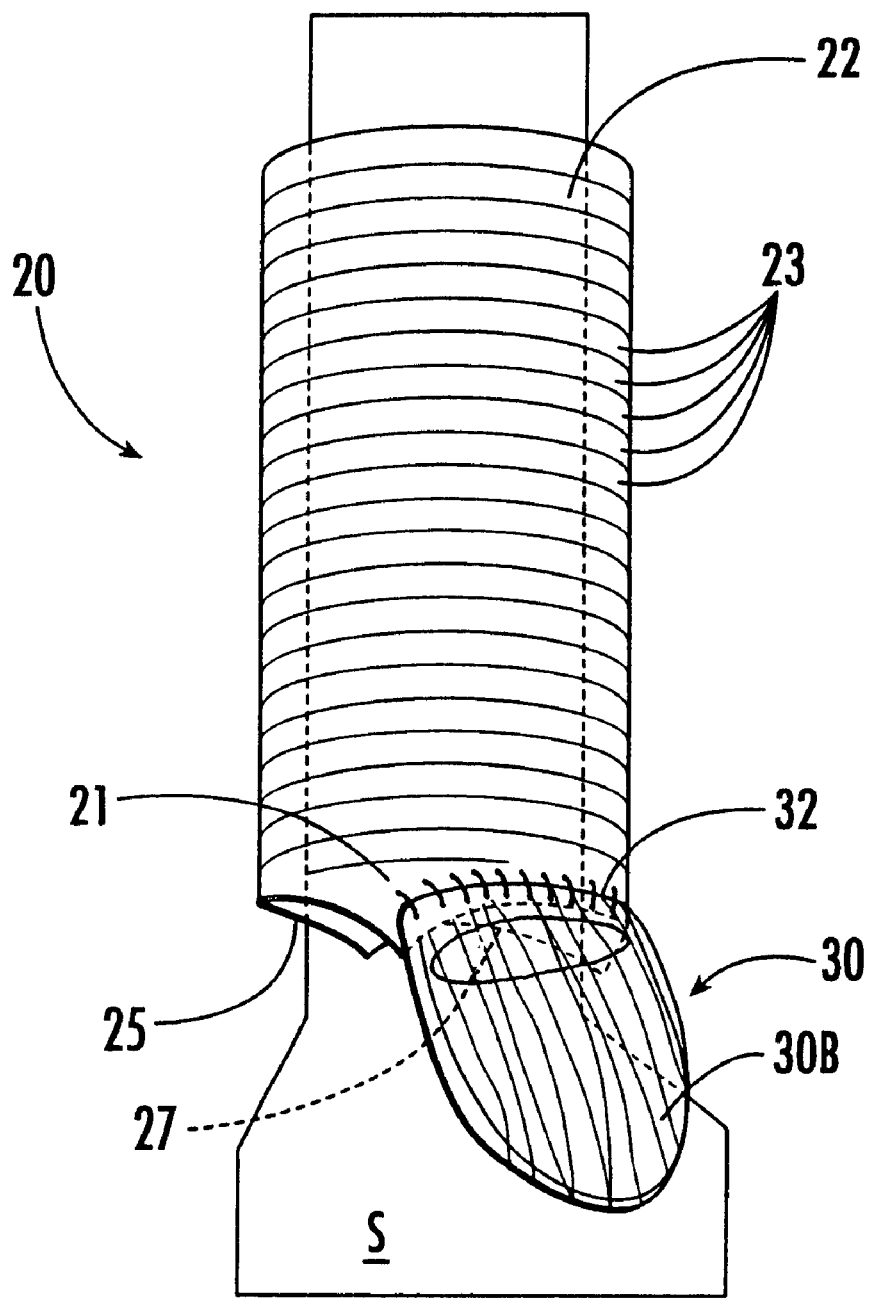
FIG. 2 is a perspective view of the aortic root prosthesis shown in FIG. 1 during assembly.
Figure 3:
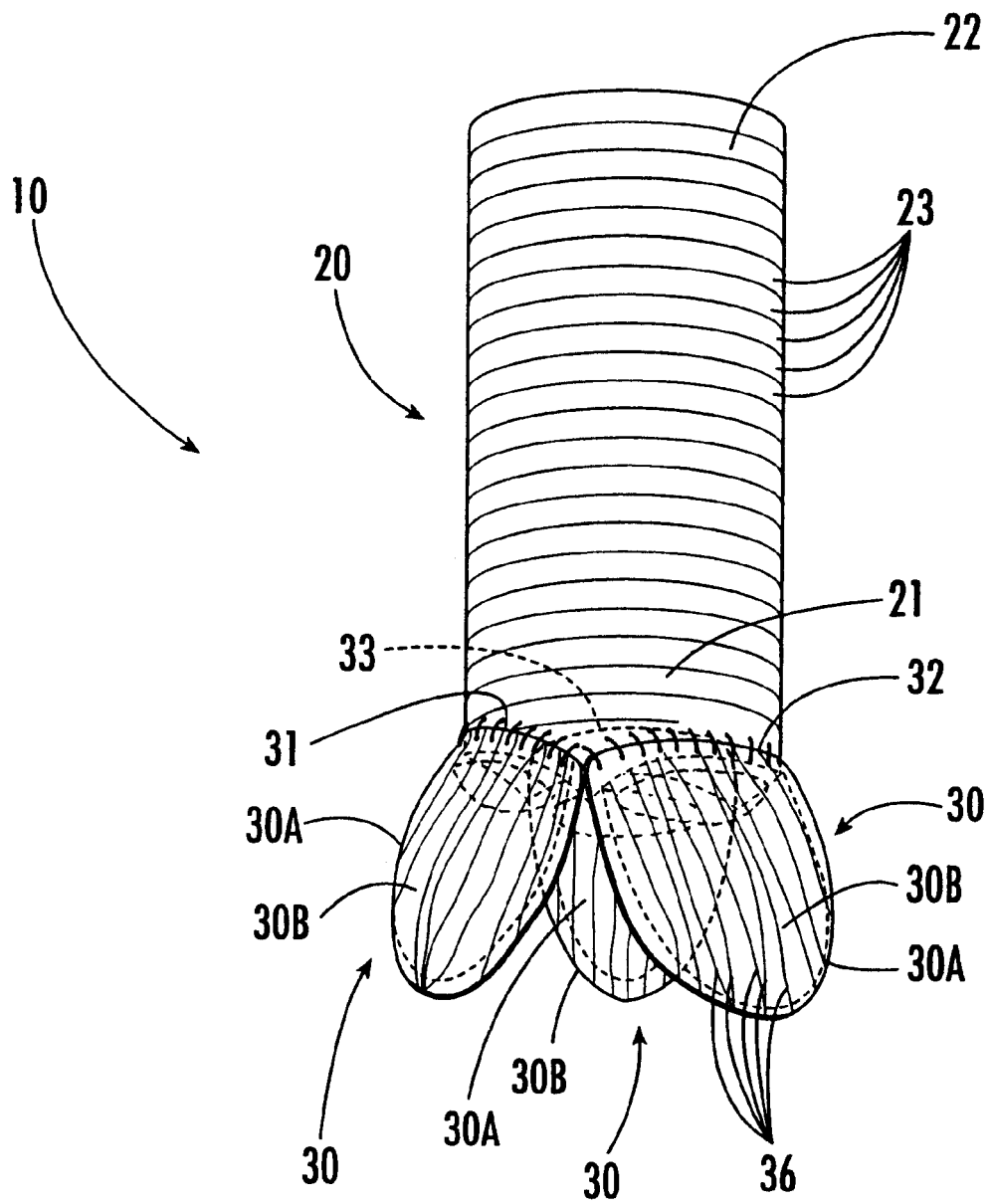
FIG. 3 is a side view elevation of the aortic root prosthesis shown in FIGS. 1 and 2 after assembly.

FIG. 2 also shows the aortic root prosthesis 10 during assembly. As is shown in FIG. 2, a syringe cover "S" is inserted into and through the tube 20, and provides support to the tube 20 as the aortic root prosthesis 10 is being assembled. A sinus 30 is then attached to the proximal end 21. The sinus 30 is attached to the proximal end 21 by stitching the sinus edge 35 to scalloped edge 26 using a running suture beginning in the middle of scalloped edge 26, thereby creating sino-tubular junction 32. FIG. 3 shows an assembled aortic root prosthesis 10 with the three sinuses 30 attached to the proximal end 21 by one of three respective sino-tubular junctions 31, 32 or 33.

Figure 4:
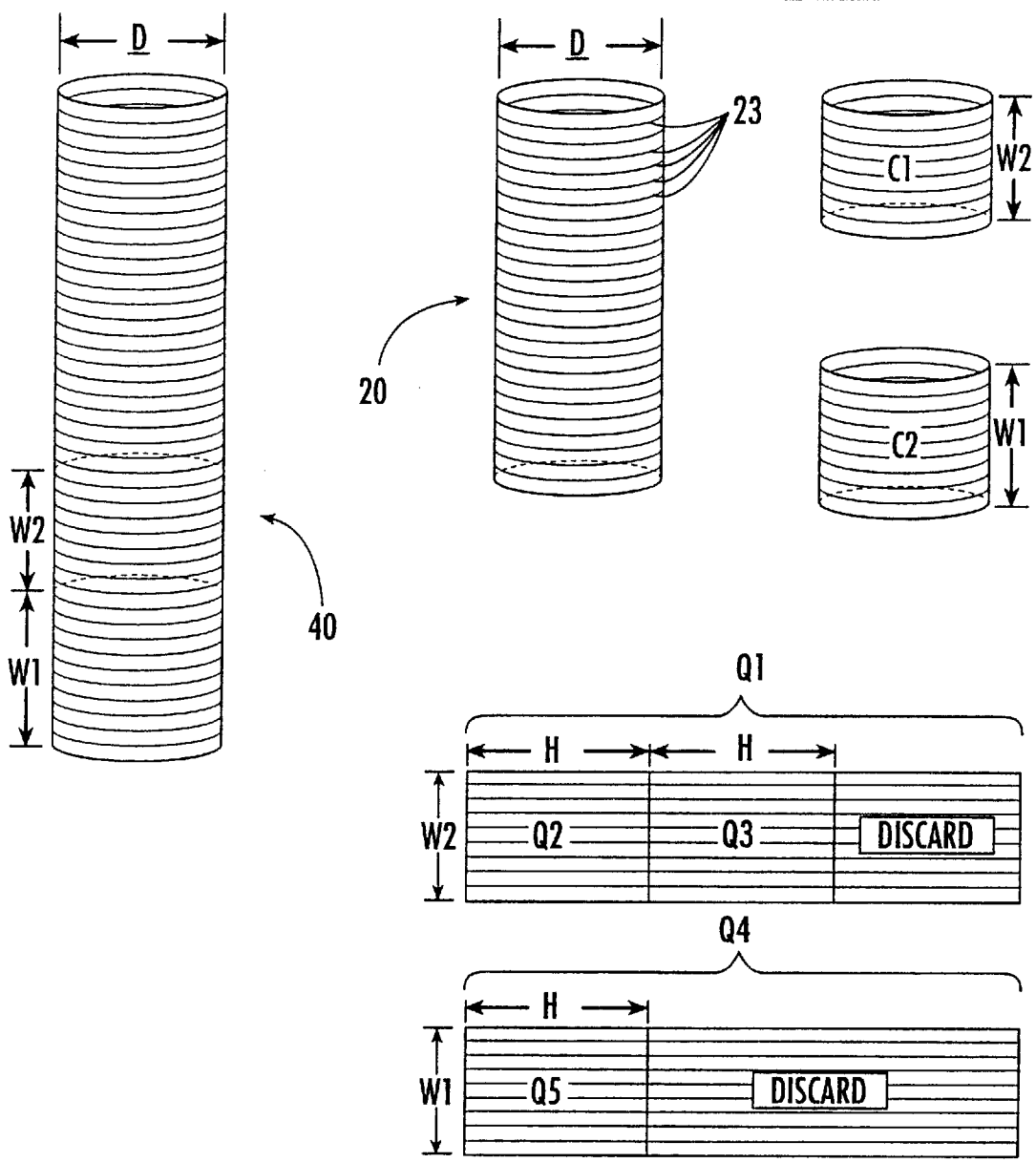
FIG. 4 is a schematic-flow diagram view of an aortic root prosthesis showing assembly steps according to another embodiment of the invention.
Figure 4:
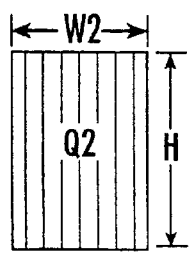
Figure 4:
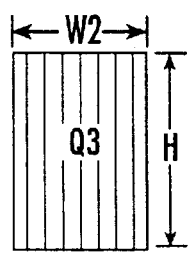
Figure 4:
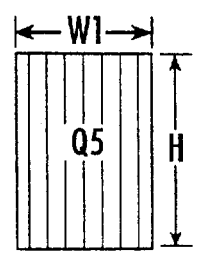

Referring now to FIGS. 4, 5, 6, 7, and 8, detailed views of the tube 20 and sinuses 30 are shown during assembly. As is shown in FIG. 4, the aortic root prosthesis 10 is formed from a cylindrical fabric tube, which is shown generally at reference numeral 40. The tube 40 has a diameter "D" equal to the diameter of the aortic valve to be spared, which is preferably between 18 to 30 millimeters. Two lengths W1 and W2 are cut from the tube 40, thereby creating, first, second and third cylindrical fabric tubes 20, C1 and C2, respectively. Lengths W1 and W2 are preferably measured in millimeters. As shown in FIG. 1, tube 20 forms the fabric aortic root having proximal and distal ends 21 and 22, respectively.

Referring again to FIG. 4, tube C1 is cut open lengthwise to form a first quadrilateral Q1. Second and third quadrilaterals Q2 and Q3, respectively, each having equal heights H, are then cut from the first quadrilateral Q1. The heights H are preferably measured in millimeters, and are preferably equal to the diameter D plus 4 millimeters (H=D+4). Quadrilaterals Q2,and Q3 are used to form respective first and second sinuses 30.

Next, cylinder C2 is cut open lengthwise to create a fourth quadrilateral Q4. A fifth quadrilateral Q5, which has a height H equal to the heights H of quadrilaterals Q2 and Q3, is cut from quadrilateral Q4, and is used to form the third sinus 30.

Figure 5A:
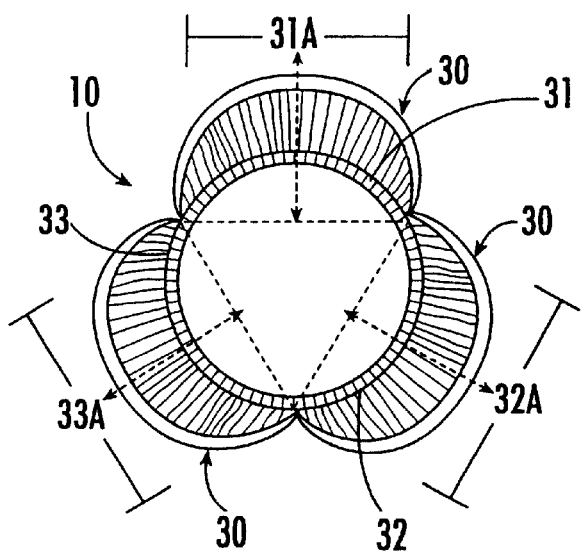
FIG. 5A is a perspective view of an aortic root prosthesis according to one embodiment of the invention.
Figure 5B:
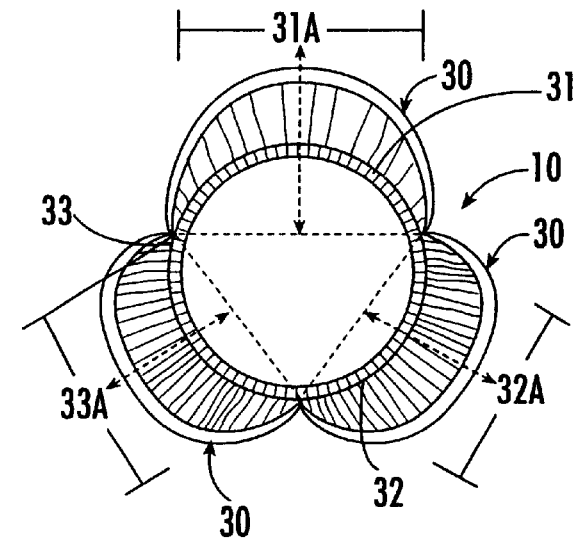
FIG. 5B is a perspective view of an aortic root prosthesis according to one embodiment of the invention.
Figure 5C:
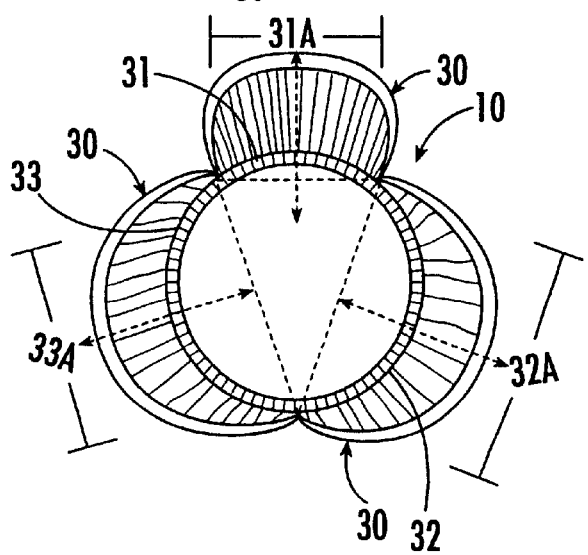
FIG. 5C is a perspective view of an aortic root prosthesis according to one embodiment of the invention.

Quadrilaterals Q2, Q3 and Q5 are then used to assemble first, second and third respective sinuses 30 for one of three possible Embodiments I, II or III, of the aortic root prosthesis 10. FIG. 5 shows Embodiments I, II and III, with each Embodiment positioned to illustrate the manner in which the sinuses 30 are attached to the proximal end 21 of the tube 20 to form the sino-tubular junctions 31, 32 and 33 and respective intercommissural distances 31A, 32A and 33A. As is shown in FIG. 5, each Embodiment I, II or III forms an aortic root prosthesis 10 having three respective sino-tubular junctions 31, 32, and 33, spaced at respective intracommissurial distances 31A, 32A and 33A. As is shown in FIG. 5A, Embodiment I preferably has three equally-spaced intracommissurial distances 31A, 32A and 33A. As is shown in FIG. 5B, Embodiment II preferably has an intracommissurial distance 31A which is larger than intracommissurial distances 32A and 33A. As is shown in FIG. 5C, Embodiment III preferably has an intracommissurial distance 31A which is smaller than intracommissurial distances 32A and 33A.

Embodiments I, II and III are represented by the following formulas:

Embodiment I $$W1=W2=H \qquad \text{I}$$

W1 corresponds to the widths of the first sinus 30 and of sino-tubular junction 31, and W2 corresponds to the widths of the second and third respective sinuses 30 and of respective sino-tubular junctions 32 and 33.

Embodiment II $$W1=H+4$$
$$W2=H-2 \qquad \text{II}$$

W1 corresponds to the width of the first sinus 30 and of sino-tubular junctions 31, and W2.corresponds to the widths of the second and third respective sinuses 30 and of respective sino-tubular junctions 32 and 33.

Embodiment III $$W1=H-4$$
$$W2=H+2 \qquad \text{III}$$

W1 corresponds to the width of the first sinus 30 and of sino-tubular junctions 31, and W2 corresponds to the widths of the second and third respective sinuses 30 and of respective sino-tubular junctions 32 and 33.

The sinus height H is equal in Embodiments I, II and III.

As shown in FIG. 4, in order to form the first, second and third sinuses 30, respective quadrilaterals Q2, Q3 and Q5 are first rotated 90 degrees so that the Z-folds 23 are positioned longitudinally with respect to the vertical axis of each quadrilateral Q2, Q3 and Q5, thereby forming Z-folds 36 of the sinuses 30.

Figure 6:
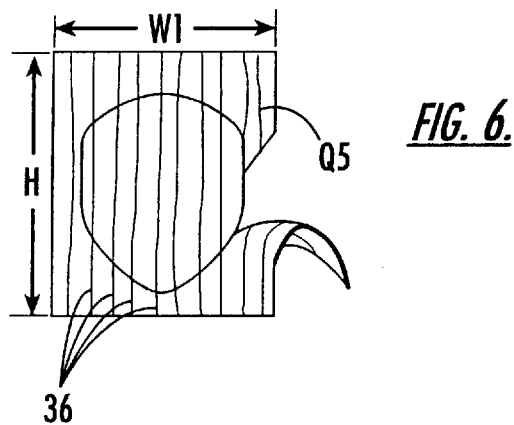
FIG. 6 is a perspective view of a sinus according to an embodiment of the invention during assembly.
Figure 7:
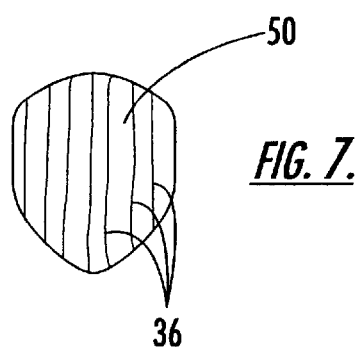
FIG. 7 is a front view of the sinus shown in FIG. 6 and during assembly.
Figure 8:
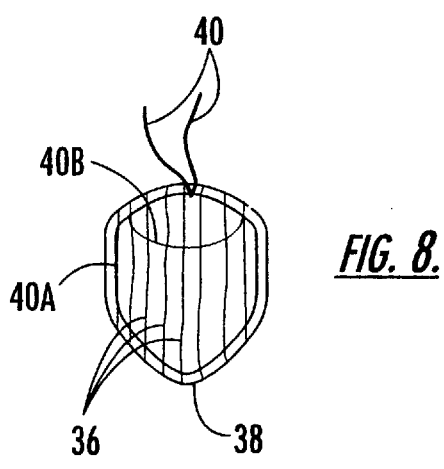
FIG. 8 is a front view of the sinus shown in FIGS. 6 and 7 during assembly

FIGS. 6, 7, 8 and 9 show the steps necessary to form a completed sinus 30. As is shown in FIG. 6 and using Quadrilateral Q5 as an example, excess fabric is trimmed from around the edges of Quadrilateral Q5, to form a general sinus shape 50, which is shown in FIG. 8. Trimming the excess fabric reduces the height H and width W1 by at least two millimeters.

Figure 9:
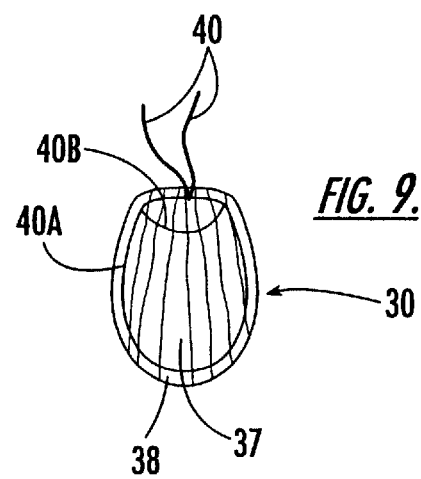
FIG. 9 is a front view of the sinus shown in FIGS. 6, 7, and 8 after assembly.
Figure 10:
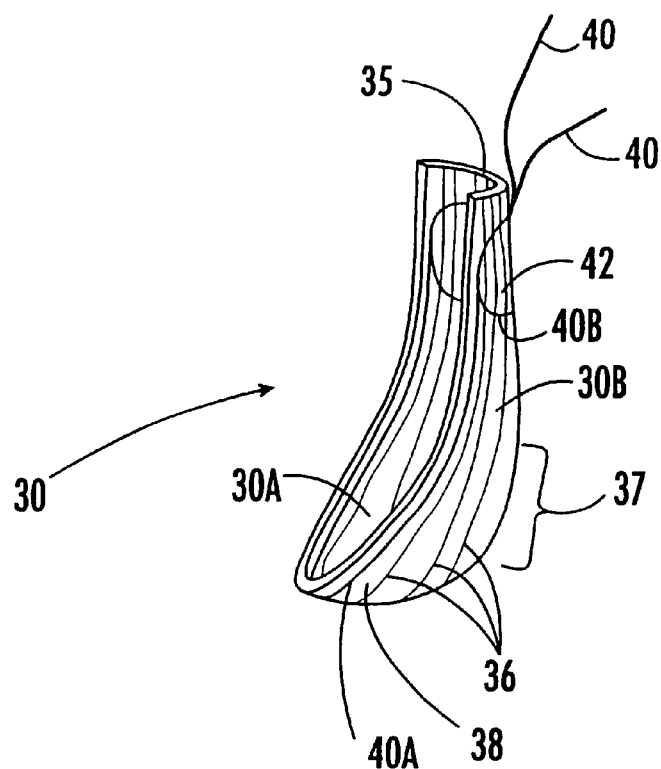
FIG. 10 is a perspective view of the sinus shown in FIGS. 6 , 7 , 8 and 9 after assembly.

Referring now to FIGS. 8, 9 and 10, a convex contour 37 is then formed by creating a seam 39 using at least one purse string 40 stitched around the sinus 30 to form first and second respective loops, 40A and 40B, which are gathered to form the contour 37. The phrase "purse string" is a term well-known in the art used to describe the process of gathering a suture in a manner similar to that of pulling a drawstring on a purse or handbag closed. As is shown in FIG. 10, gathering the loops 40A and 40B in this manner deflects the convex contour downwardly toward the end 38 of the sinus 30. The loop 40A is preferably stitched approximately 2 millimeters from the edge of the sinus 30. The purse string 40 is preferably formed using 4-0 polypropylene suture.

The steps shown in FIGS. 6, 7,8, 9 and 10 are then repeated using quadrilaterals Q2 and Q3 to form respective second and third sinuses 30.

Figure 11:
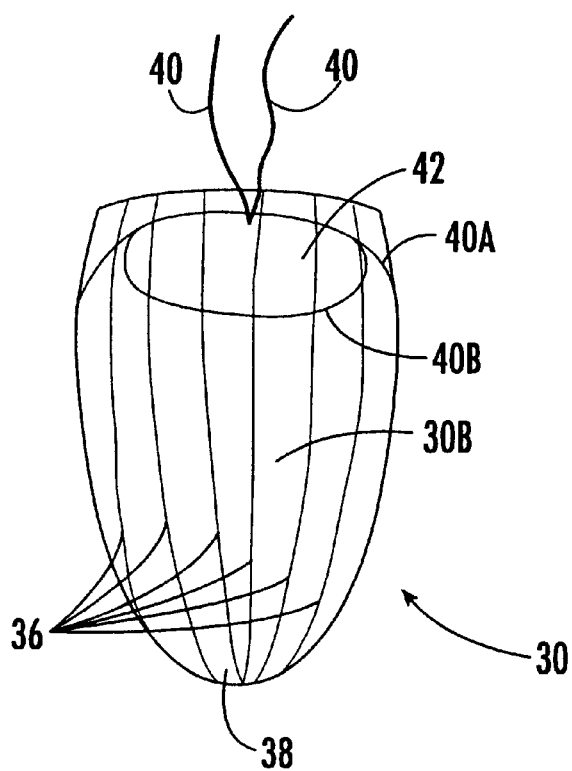
FIG. 11 is a front view of the sinus shown in FIGS. 9 and 10.

FIGS. 10 and 11 show perspective and front views, respectively, of an assembled sinus 30. The sinus 30 has inner and outer walls 30A and 30B, respectively, and a sinus edge 35. A plurality of integrally-formed Z-folds 36 extends along the vertical axis of the sinus 30. The Z-folds 36 allow the sinus 30 to be stretched laterally. Furthermore, the Z-folds 36 are oriented in the direction of blood flow, and are thus adapted to allow smooth formation of vortices in the space behind a biological aortic leaflet as blood flows therethrough. Orienting the Z-folds 36 in this manner also reduces the likelihood that thrombus and emboli will form in the aorta. By forming the contour 37 in each sinus 30, a circumferentially oriented, elliptically-shaped cross-section 42 is created, which allows stress to be shared between the leaflets and the sinuses 30. The creation of the cross-section 42 and contour 37 in each sinus is important because it differs from prior art tubular prostheses, in which a significant stress concentration occurs at the leaflet-graft junction. Absence of stress concentration is necessary for longevity of the leaflets, and is achieved by using the contoured shape of the present invention in each of the sinuses 30.

Figure 12:
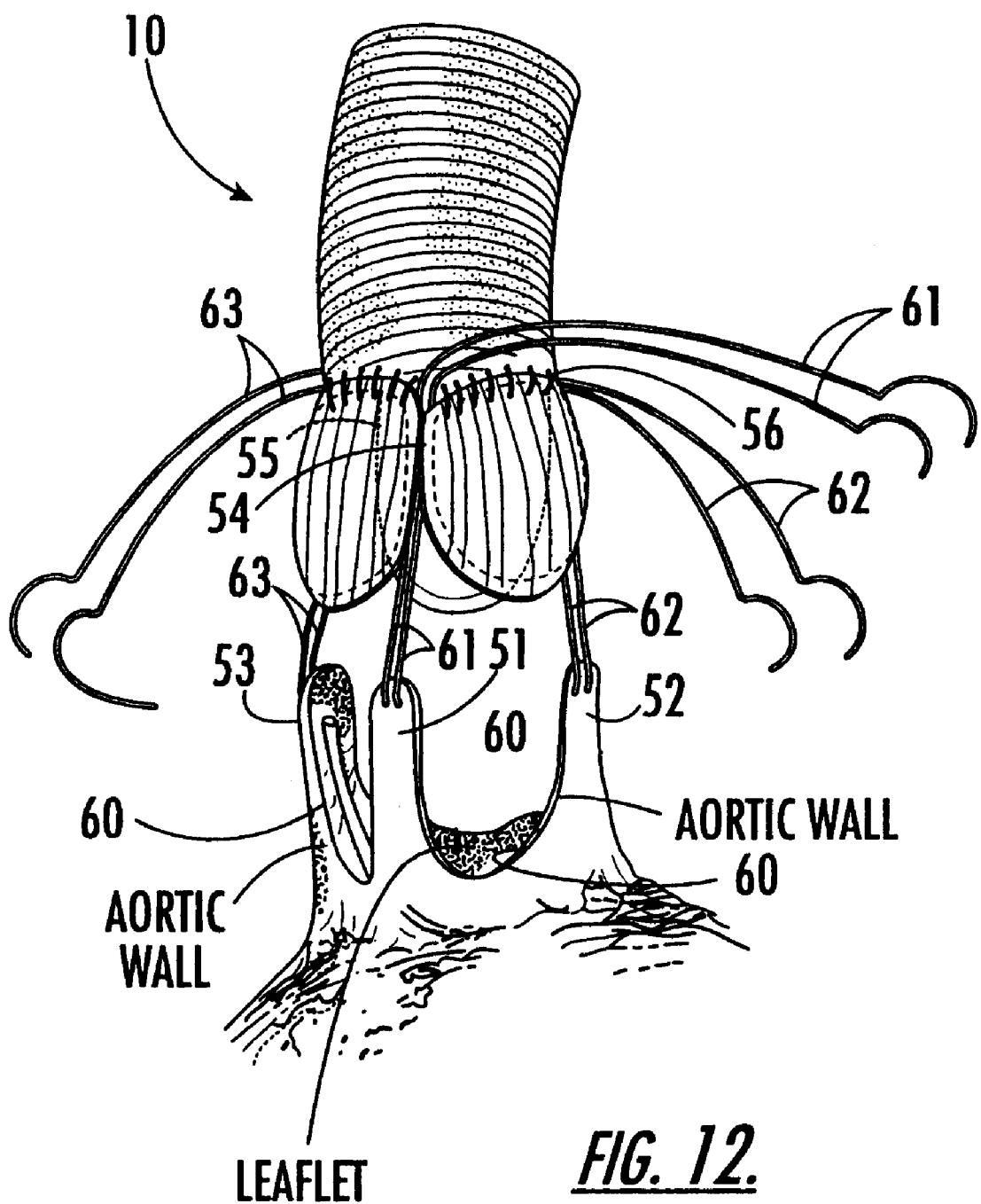
FIG. 12 is a perspective view of an aortic root prosthesis according to an embodiment of the invention during implantation into a patient.
Figure 13:
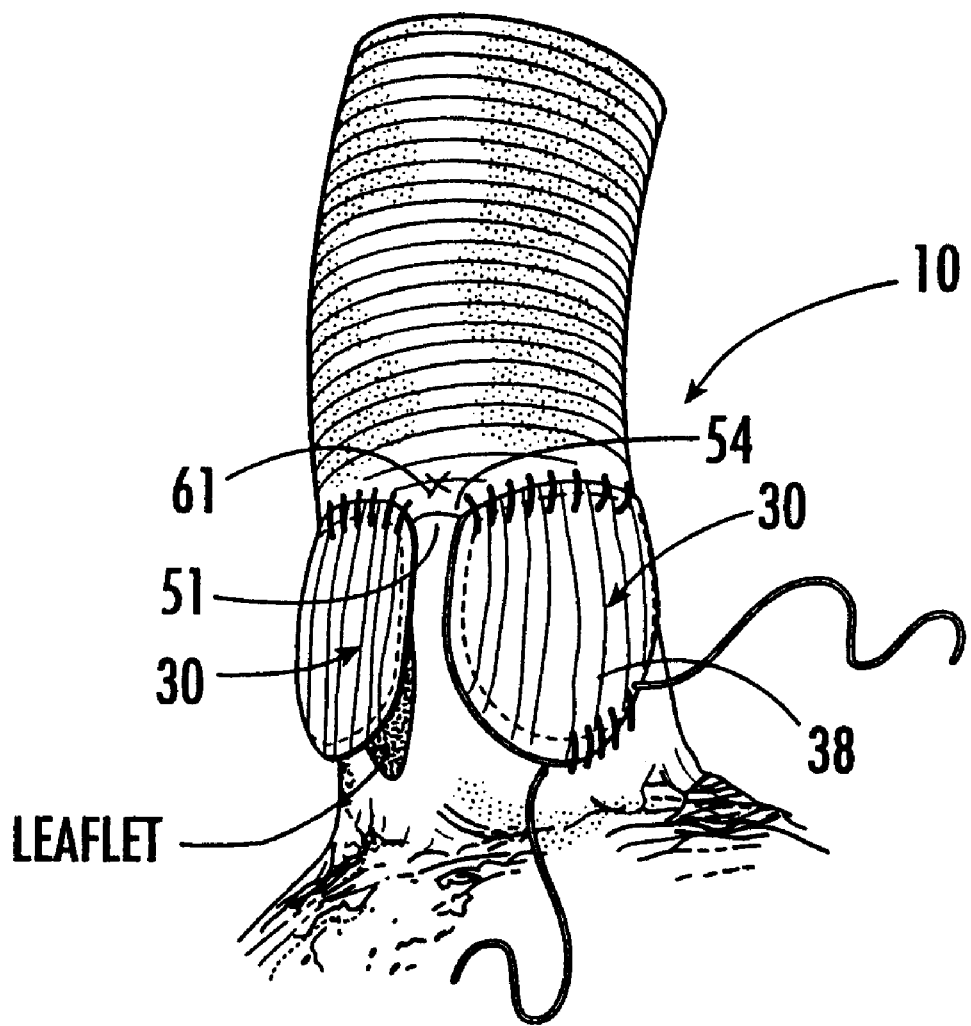
FIG. 13 is a perspective view of the aortic root prosthesis shown in FIG. 12 during implantation into a patient.
Figure 14:
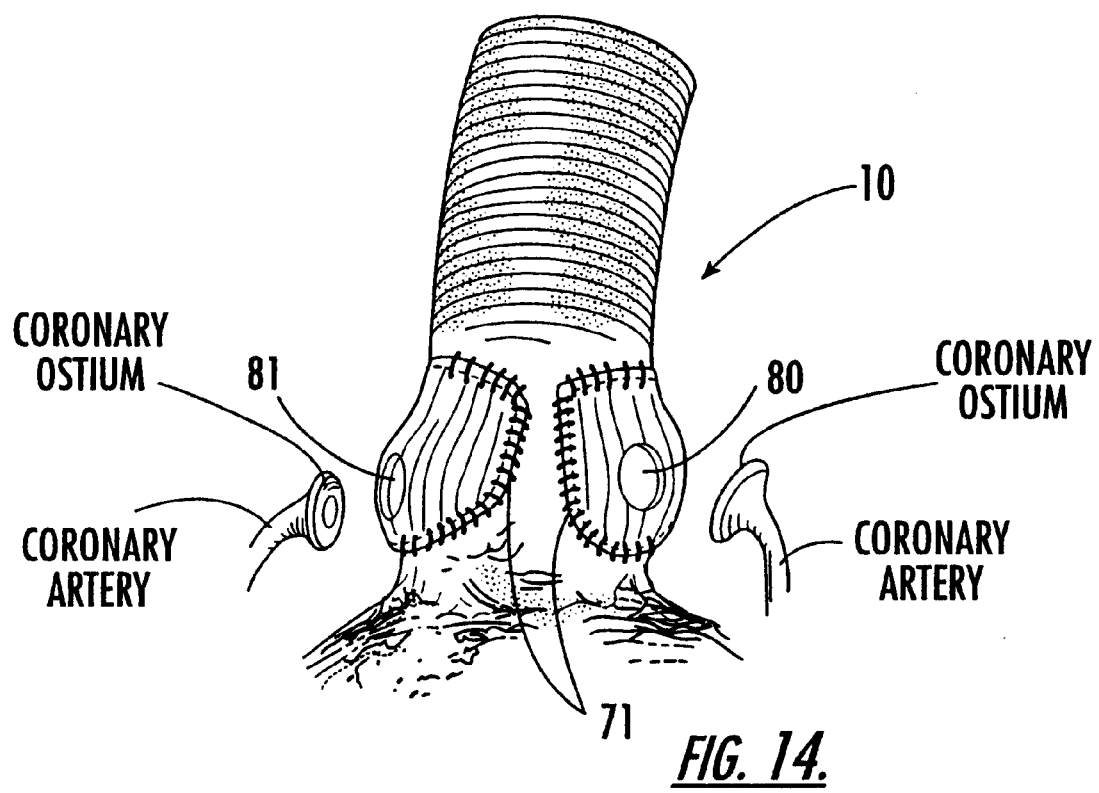
FIG. 14 is a perspective view of coronary arteries being sutured to the aortic root prosthesis shown in FIGS. 12 and 13.

Referring now to FIGS. 12, 13, 14 and 15, the aortic root prosthesis 10 is shown during and after implantation. As is shown in FIG. 12, a scalloped edge 60 is formed by cutting along the periphery of the aortic valve, thereby leaving approximately 2–3 millimeters of the aortic wall along the scalloped edge 60. Next, orientation sutures 61, 62, and 63 are stitched at aortic commissures 51, 52 and 53, respectively. The orientation sutures 61, 62 and 63 are tied to the aortic root prosthesis 10 at respective sino-tubular commissures 54, 55, and 56, which produces suspension of the aortic valve. FIG. 13 shows orientation suture 61 tied and attaching aortic commissure 51 to sino-tubular commissure 54 Starting at the center of end 38 of the sinus 30, each sinus 30 is then sutured to the aortic wall around the periphery of the aortic valve, thereby creating a leaflet attachment line 71, which is shown in FIG. 14.

Figure 15:
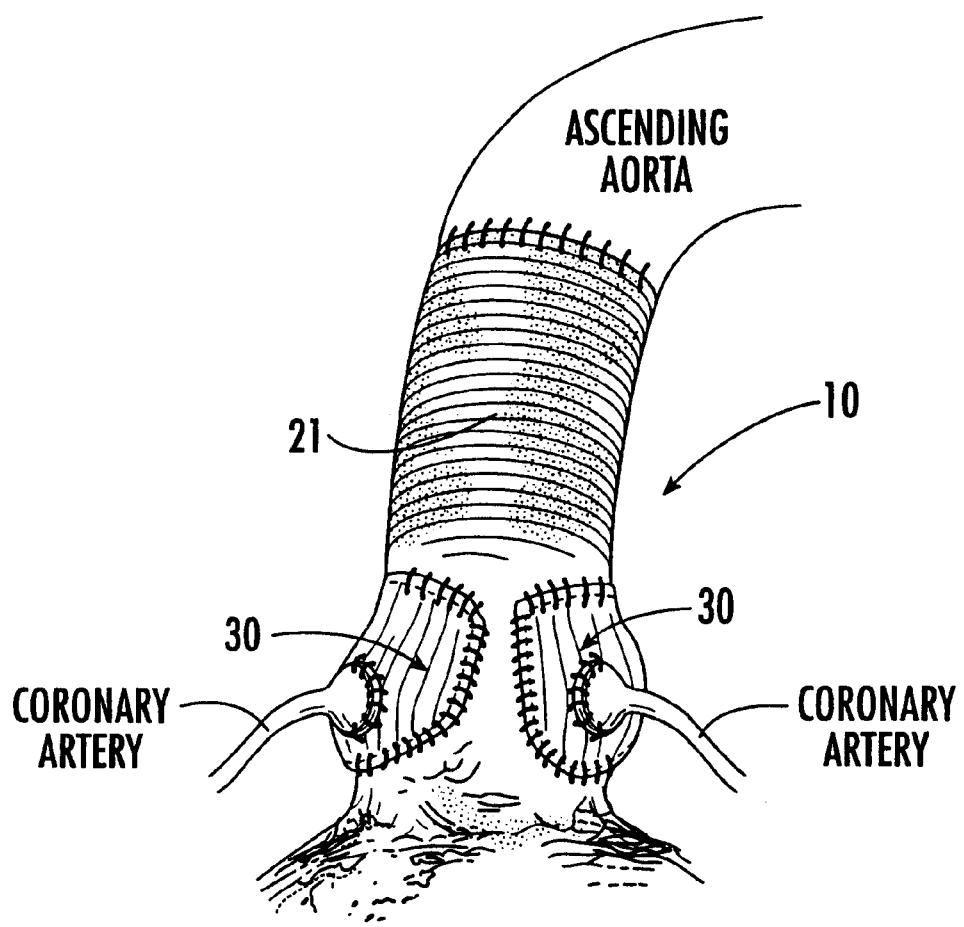
FIG. 15 is a perspective view of the aortic root prosthesis shown in FIGS. 12, 13, and 14 after implantation into a patient.

FIGS. 14 and 15 also show the coronary arteries being attached to two of three of the sinuses 30. Two holes 80 and 81, respectively, are cut through and defined by, each of the two sinuses. Each coronary ostium is then sutured to a respective sinus 30 around the periphery of each respective hole 80 or 81, which allows blood to flow freely therethrough. As is shown in FIG. 15, the distal end 21 is then sutured to the ascending aorta, thereby completing an aortic root graft having compliance and geometry which mimics that of a biological aortic root, and which promotes normal physiological function of a biological aortic valve.

Figure 16:
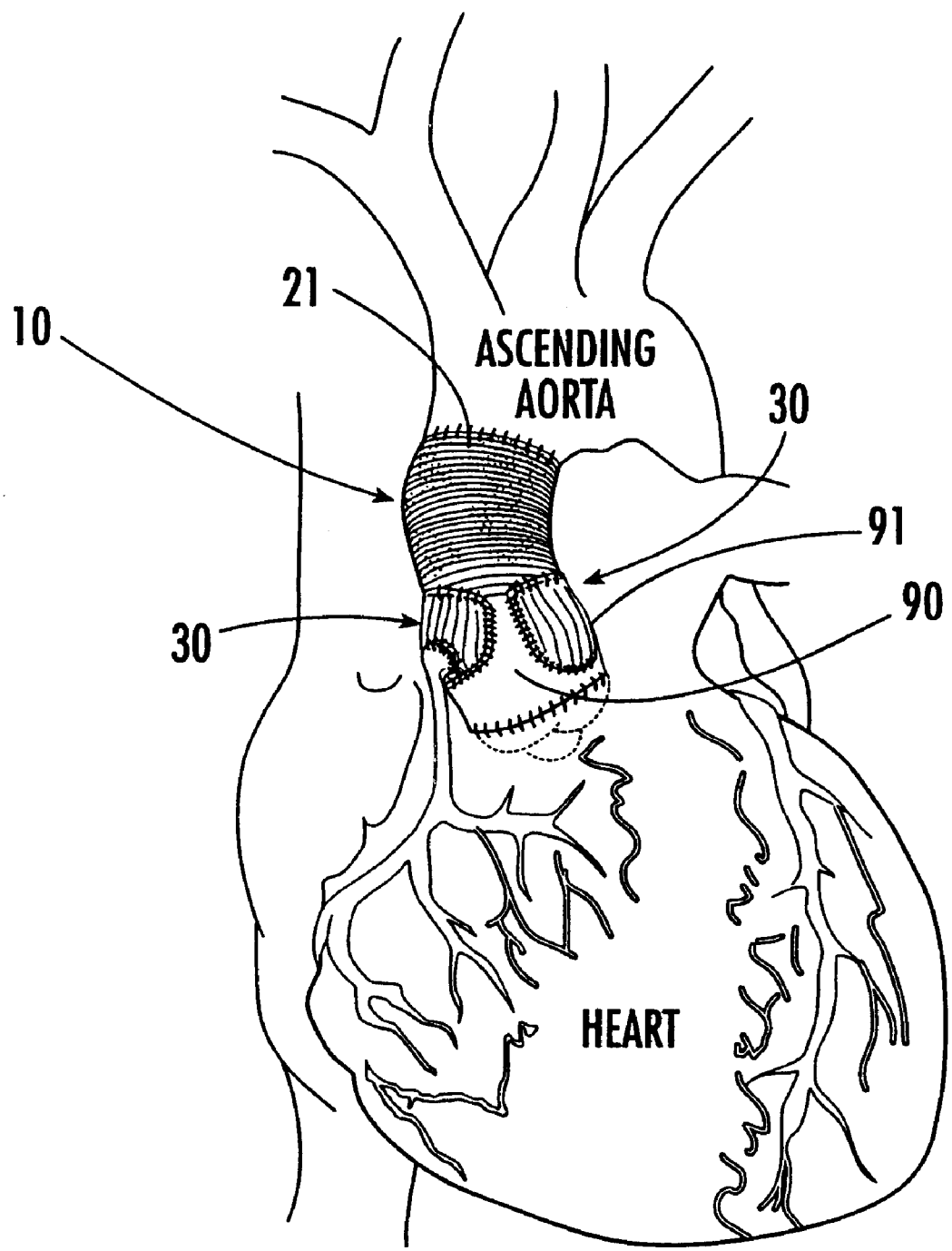
FIG. 16 is a perspective view of an aortic root prosthesis implanted with a stentless bioprosthetic valve according to another embodiment of the invention.

Referring now to FIG. 16, the aortic root prosthesis 10 is shown with a stentless bioprosthetic aortic valve 90 after implantation. The stentless bioprostetic aortic valve 90 is preferably comprised of animal tissue. As is shown in FIG. 16, each sinus 30 is sutured to the valve 90 around the periphery of the valve 90, thereby creating a leaflet attachment line 91. The distal end 21 is then sutured to the ascending aorta.

Figure 17:
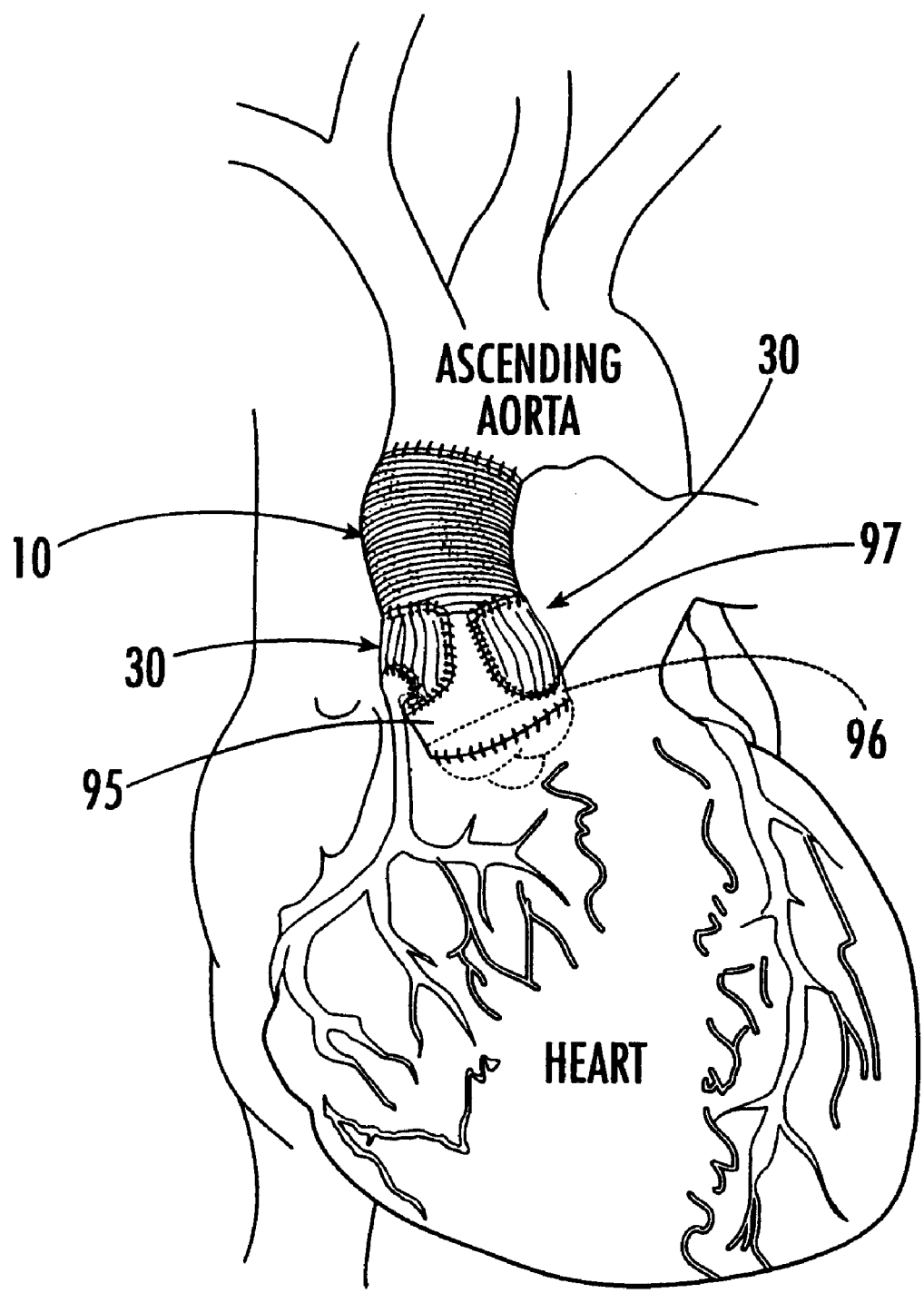
FIG. 17 is a perspective view of an aortic root prosthesis implanted with a stented bioprosthetic valve according to another embodiment of the invention.

FIG. 17 shows the aortic root prosthesis 10 implanted with a stented bioprosthetic aortic valve 95. The stented bioprostetic aortic valve 95, is preferably comprised of animal tissue, and includes a stent 96, which is shown drawn in phantom. The stent 96 allows the valve 95 to be securely sutured to the heart. The stent 96 preferably comprises a ring made of plastic or a similar material. As is shown in FIG. 17, each sinus 30 is sutured to the valve 95 around the periphery of the valve 95, thereby creating a leaflet attachment line 97. The distal end 21 is then sutured to the ascending aorta.

An aortic root prosthesis is shown above. Various details of the invention may be changed without departing from its scope. Furthermore, the foregoing description of the preferred embodiments of the invention and the best mode for practicing the invention are provided for the purpose of illustration only and not for the purpose of limitation—the invention being defined by the claims.

We claim:

1. An aortic root prosthesis for being implanted into a patient during a valve sparing surgery as a replacement for a biological aortic root segment of an ascending aorta, comprising:

(a) a hollow, annular tube having proximal and distal ends, and an inner and outer wall, said distal end adapted for being attached to the ascending aorta; and (b) a plurality of sinuses circumferentially connected to the proximal end of said tube, each of said sinuses adapted for being attached to an aortic wall and including:

(i) contouring means for imparting a convex contour to an outer wall of the sinus to thereby create a space between an open leaflet of an aortic valve and the respective sinus to prevent impact between the open leaflet and an inner wall of the sinus; and (ii) a plurality of Z folds formed in and extending along the vertical axis of the sinus parallel to the longitudinal axis of the tube for allowing the sinus to be stretched laterally.

2. An aortic root prosthesis according to claim 1, wherein said tube and said sinuses are comprised of a polyester fabric.

3. An aortic root prosthesis according to claim 2, and including a plurality of Z folds formed in and extending circumferentially around the tube.

4. An aortic root prosthesis according to claim 3, wherein said contouring means comprises at least one purse string stitched around each sinus to form two concentric loops, said loops gathered to form a tear-drop-shaped sinus, wherein said convex contour is deflected downwardly toward the end of the sinus and remote from the tube.

5. An aortic root prosthesis according to claim 4, wherein at least one of the loops is stitched approximately two millimeters from the periphery of each sinus.

6. An aortic root prosthesis according to claim 5, wherein said purse string comprises 4-0 polypropylene suture.

7. An aortic root prosthesis according to claim 6, wherein the proximal end of the tube includes an edge scalloped at a depth of at least two millimeters, thereby permitting formation of a sino-tubular junction where each sinus connects with the proximal end of the tube along the edge.

8. An aortic root prosthesis according to claim 7, wherein each sinus is connected to the proximal end of the tube by respective sino-tubular junctions spaced at equal intercommissural distances.

9. An aortic root prosthesis according to claim 7, wherein each sinus is connected to the proximal end of the tub by respective sino-tubular junctions, and wherein each of said sino-tubular junctions is spaced at a first, second and third intercommissural distance, respectively, and wherein said first intercommissural distance is smaller than said second and third intercommissural distances.

10. An aortic root prosthesis according to claim 7, wherein each sinus is connected to the proximal end of the tube by respective sino-tubular junctions, wherein each of said sino-tubular junctions is spaced at a first, second and third intercommissural distance, respectively, and wherein the first intercommissural distance is larger than the second and third intercommissural distances.

11. An aortic root prosthesis according to claim 8, 9 or 10, wherein the valve comprises a stented bioprosthetic valve.

12. An aortic root prosthesis according to claim 8, 9 or 10, wherein the valve comprises a stentless bioprosthetic valve.

* * * * *